(12) United States Patent
Burnard et al.

(10) Patent No.: US 10,364,914 B2
(45) Date of Patent: Jul. 30, 2019

(54) VALVE DEVICE, A DELIVERY SYSTEM INCLUDING SAME AND METHOD

(71) Applicant: B. Braun Medical Inc., Bethlehem, PA (US)

(72) Inventors: Edwin Burnard, Bethlehem, PA (US); Murat Ozgu, Bethlehem, PA (US); Benjamin Loomis, Bethlehem, PA (US)

(73) Assignee: B. BRAUN MEDICAL INC., Bethlehem, PA (US)

( * ) Notice: Subject to any disclaimer, the term of this patent is extended or adjusted under 35 U.S.C. 154(b) by 1063 days.

(21) Appl. No.: 14/500,581

(22) Filed: Sep. 29, 2014

(65) Prior Publication Data

US 2016/0089492 A1 Mar. 31, 2016

(51) Int. Cl.
| | |
|---|---|
| A61M 5/168 | (2006.01) |
| F16K 35/04 | (2006.01) |
| F16K 15/18 | (2006.01) |
| A61M 39/22 | (2006.01) |
| A61M 39/24 | (2006.01) |
| A61M 39/26 | (2006.01) |

(52) U.S. Cl.
CPC .......... *F16K 35/04* (2013.01); *A61M 39/225* (2013.01); *A61M 39/24* (2013.01); *F16K 15/18* (2013.01); *A61M 5/16881* (2013.01); *A61M 2039/2466* (2013.01)

(58) Field of Classification Search
CPC ................. A61M 39/225; A61M 39/24; A61M 5/16881; A61M 2039/2466; A61M 2039/261; A61M 2039/262; Y10T 137/7877; Y10T 137/7876; Y10T 137/2605; Y10T 137/262; F16K 15/18; F16K 15/185; F16K 35/04
See application file for complete search history.

(56) References Cited

U.S. PATENT DOCUMENTS

| | | | | |
|---|---|---|---|---|
| 3,664,339 | A | * | 5/1972 | Santomieri .......... A61M 5/1411 137/399 |
| 4,038,983 | A | * | 8/1977 | Mittleman ............ F16K 15/147 604/124 |
| 4,464,179 | A | * | 8/1984 | Barger ................ A61M 39/225 604/250 |

(Continued)

*Primary Examiner* — Jenna Zhang
(74) *Attorney, Agent, or Firm* — Kenealy Vaidya LLP

(57) ABSTRACT

The disclosed subject matter relates to a valve device that includes a valve member located within a housing in which the valve member's operation can be bypassed. For example, the valve device can include a bypass device that has an input structure, a motion conversion structure, and an output structure. The input structure can include a portion configured to resiliently deform if a valve opening input force is applied to the input structure in an input direction. The motion conversion structure can be configured to convert the valve opening input force into motion of the output structure in an output direction that is non-parallel to the input direction. The output structure can be configured to move the valve member (e.g., from a closed state to an opened state in order to bypass normal valve operation) if the motion conversion structure is displaced in the input direction. The valve device can be used in various manners, and is particularly suitable for use in a patient fluid delivery system.

28 Claims, 13 Drawing Sheets

(56) References Cited

U.S. PATENT DOCUMENTS

| | | | |
|---|---|---|---|
| 4,535,820 A | 8/1985 | Raines | |
| 4,683,916 A * | 8/1987 | Raines | A61M 39/26 137/854 |
| 5,226,886 A | 7/1993 | Skakoon et al. | |
| 5,308,333 A | 5/1994 | Skakoon | |
| 5,439,451 A * | 8/1995 | Collinson | A61M 39/26 137/614.18 |
| 5,697,904 A | 12/1997 | Raines et al. | |
| 5,699,821 A * | 12/1997 | Paradis | A61M 39/02 137/1 |
| 6,039,302 A * | 3/2000 | Cote, Sr. | A61M 39/26 251/149.1 |
| 7,150,727 B2 | 12/2006 | Cise et al. | |
| 7,367,963 B2 | 5/2008 | Cise et al. | |
| 7,510,545 B2 * | 3/2009 | Peppel | A61M 39/045 604/256 |
| 7,815,612 B2 | 10/2010 | Cise et al. | |
| 7,976,513 B2 | 7/2011 | Cise et al. | |
| 2003/0050610 A1 * | 3/2003 | Newton | A61M 39/26 604/256 |
| 2006/0058740 A1 * | 3/2006 | Cise | A61M 5/142 604/247 |
| 2006/0178645 A1 * | 8/2006 | Peppel | A61M 39/045 604/249 |
| 2007/0270756 A1 * | 11/2007 | Peppel | A61M 39/02 604/167.06 |
| 2010/0076370 A1 * | 3/2010 | Howlett | A61M 5/1424 604/65 |
| 2011/0319859 A1 * | 12/2011 | Zeytoonian | A61M 39/045 604/500 |
| 2012/0130305 A1 * | 5/2012 | Bonnal | A61M 39/02 604/30 |
| 2012/0310179 A1 * | 12/2012 | Truitt | A61M 39/02 604/249 |
| 2014/0249477 A1 * | 9/2014 | Grimm | A61M 5/385 604/126 |
| 2014/0276455 A1 * | 9/2014 | Yeh | A61M 39/10 604/247 |

* cited by examiner

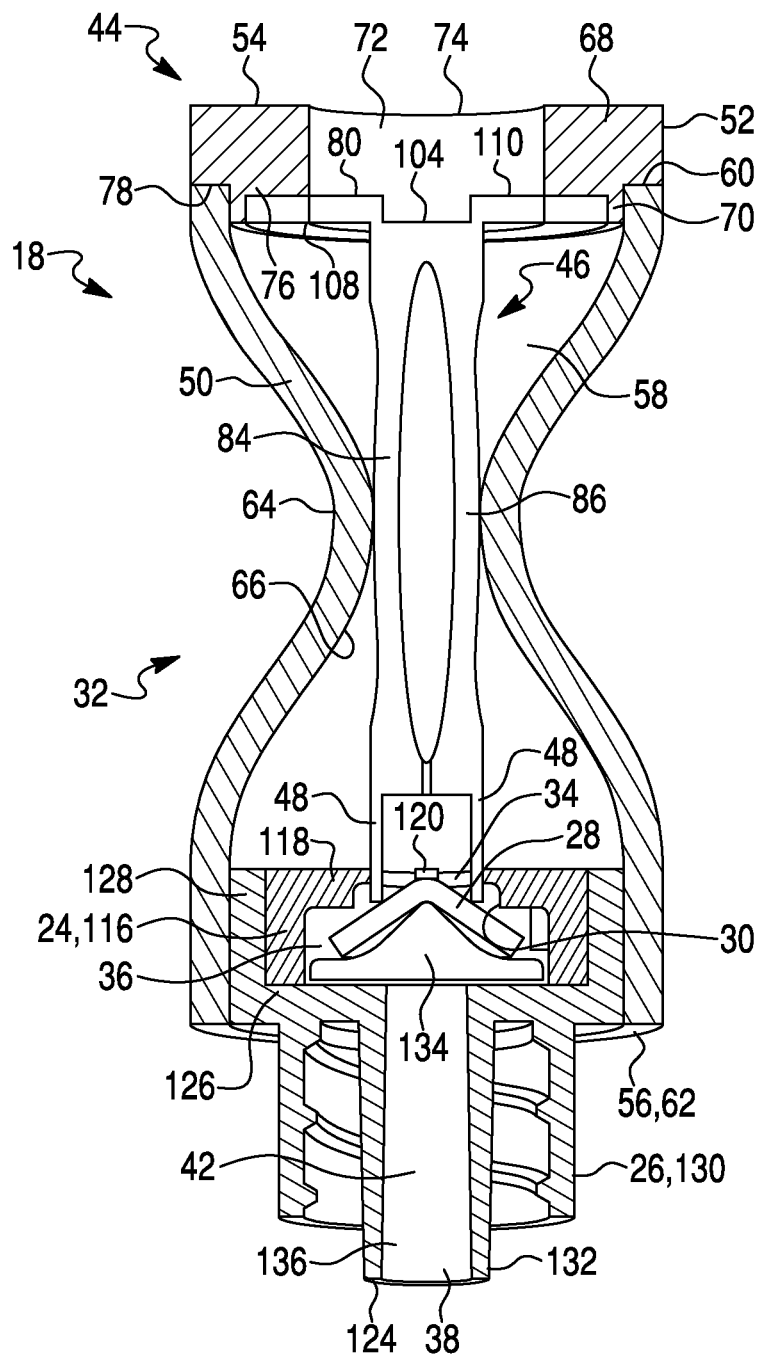

Fig. 5

Width Between Leaf Springs

| r | x | | | | | |
|---|---|---|---|---|---|---|
|  | 0.2 | 0.3 | 0.4 | 0.5 | 0.6 | 0.7 |
| 0.4 | 0.107 | 0.271 | 0.800 | | | |
| 0.45 | 0.094 | 0.229 | 0.488 | | | |
| 0.5 | 0.083 | 0.200 | 0.400 | 1.000 | | |
| 0.55 | 0.075 | 0.178 | 0.345 | 0.642 | | |
| 0.6 | 0.069 | 0.161 | 0.306 | 0.537 | 1.200 | |
| 0.65 | 0.063 | 0.147 | 0.275 | 0.469 | 0.800 | |
| 0.7 | 0.058 | 0.135 | 0.251 | 0.420 | 0.679 | 1.400 |
| 0.75 | 0.054 | 0.125 | 0.231 | 0.382 | 0.600 | 0.961 |
| 0.8 | 0.051 | 0.117 | 0.214 | 0.351 | 0.542 | 0.825 |
| 0.85 | 0.048 | 0.109 | 0.200 | 0.325 | 0.496 | 0.736 |
| 0.9 | 0.045 | 0.103 | 0.188 | 0.303 | 0.458 | 0.669 |
| 0.95 | 0.043 | 0.097 | 0.177 | 0.284 | 0.427 | 0.615 |
| 1.00 | 0.040 | 0.092 | 0.167 | 0.268 | 0.400 | 0.572 |
| 1.05 | 0.038 | 0.088 | 0.158 | 0.253 | 0.377 | 0.535 |
| 1.1 | 0.037 | 0.083 | 0.151 | 0.240 | 0.356 | 0.503 |
| 1.15 | 0.035 | 0.080 | 0.144 | 0.229 | 0.338 | 0.475 |
| 1.2 | 0.034 | 0.076 | 0.137 | 0.218 | 0.322 | 0.451 |
| 1.25 | 0.032 | 0.073 | 0.131 | 0.209 | 0.307 | 0.429 |
| 1.3 | 0.031 | 0.070 | 0.126 | 0.200 | 0.293 | 0.409 |
| 1.35 | 0.030 | 0.068 | 0.121 | 0.192 | 0.281 | 0.391 |
| 1.4 | 0.029 | 0.065 | 0.117 | 0.185 | 0.270 | 0.375 |
| 1.45 | 0.028 | 0.063 | 0.113 | 0.178 | 0.260 | 0.360 |
| 1.5 | 0.027 | 0.061 | 0.109 | 0.172 | 0.250 | 0.347 |
| 1.55 | 0.026 | 0.059 | 0.105 | 0.166 | 0.242 | 0.334 |
| 1.6 | 0.025 | 0.057 | 0.102 | 0.160 | 0.234 | 0.323 |

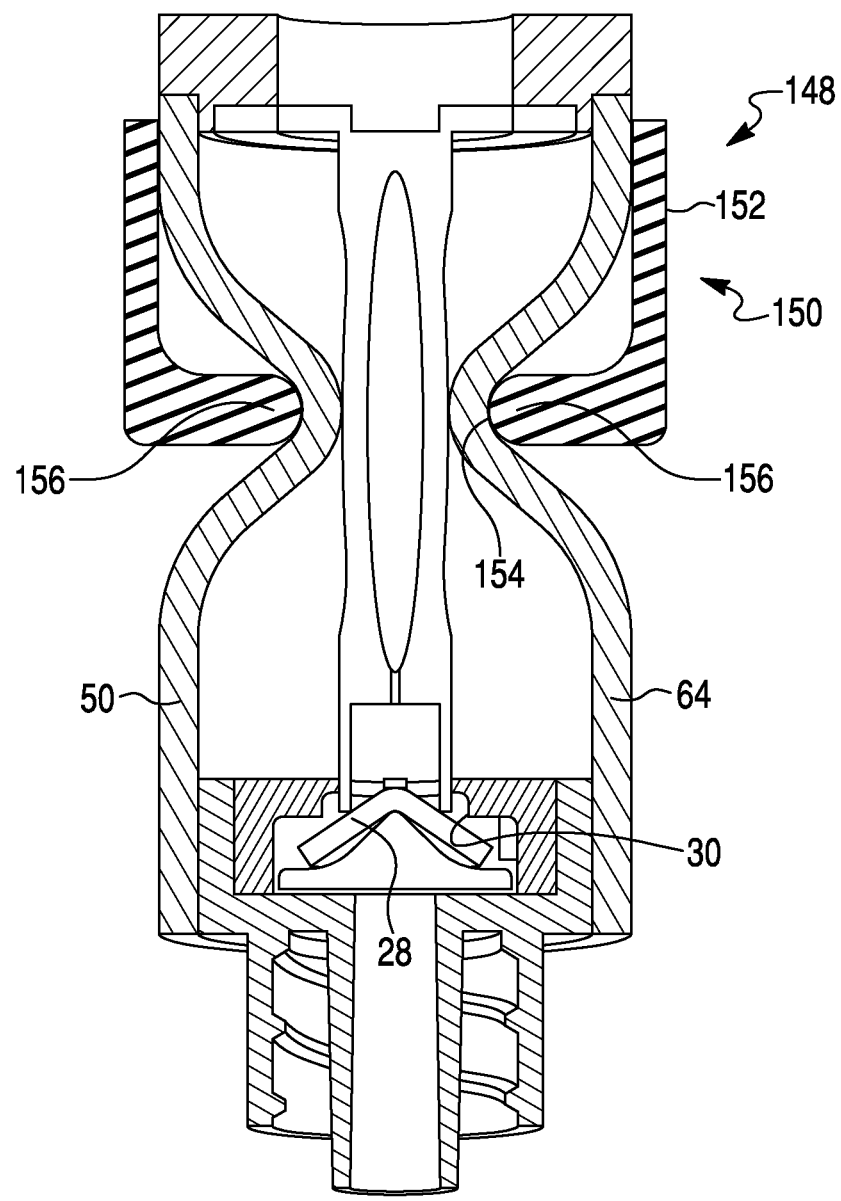

VALVE DEVICE, A DELIVERY SYSTEM INCLUDING SAME AND METHOD

BACKGROUND

1. Field

The presently disclosed subject matter relates generally to fluid flow devices, systems, and related methods, and more specifically to a valve device, fluid delivery system and method for operating the valve device to infuse fluids to a patient.

2. Description of the Related Art

A directional control valve can be used to control the direction of fluid flow from one component of a fluid system to another component of the fluid system. The directional control valve can allow fluid to pass through the directional control valve in a first direction and can prevent, or substantially prevent, the flow of fluid through the valve in a second direction that is typically a direction opposite to the first direction. The directional control valve can also limit fluid flow through the valve in the first direction.

A ball check valve is an exemplary directional control valve that includes a ball biased against a mating valve seat by a spring. The spring biases the ball against the seat to seal the valve against fluid flow in the second direction. If the fluid pressure on the upstream side of the ball is greater than the bias force applied by the spring, the fluid pressure will unseat the ball from the valve seat permitting fluid to flow through the ball check valve. The ball check valve is an example from the family of back check valves that are typically referred to as normally closed check valves because the valve member is normally biased into engagement with the seat (i.e., closed) when no fluid pressure (in either direction) is exerted against the valve member.

There may be a desire to override or bypass the normally closed check valve to permit the fluid to pass through the valve in the first direction, regardless of pressure. On other occasions, it may be desired to override or bypass the check valve to permit fluid to pass through the check valve in the second direction. Typically, the check valve is removed from the fluid system in order to accomplish either of the immediately above-described desired flows through the check valve. However, this operation can require a shut down of the fluid system until the check valve is removed and replaced with another component, such as a conduit. Once the desired bypass flow is complete, the fluid system is disassembled and the check valve is re-inserted therein.

Medical fluid delivery systems can include a normally closed back check valve in order to prevent aspiration of infusate, blood or other fluid away from the patient. Certain desired treatments for a patient can include a step in which a fluid is aspirated either away or from the patient using the fluid delivery system. In order to accomplish this step, the normally closed check valve can be removed from the fluid delivery system prior to the aspiration and then re-inserted into the fluid delivery system subsequent to the aspiration. The removal and re-insertion of the normally closed check valve can complicate the aspiration treatment through the removal and re-insertion steps.

Recently, there have been efforts to provide a bypass device that can open the normally closed back check valve without removing the check valve from the fluid delivery system. Such a bypass device can increase the versatility of the fluid system while maximizing the efficiency and sterility of the fluid system during the transition to and from the bypassed state. In addition, such a fluid system can reduce the time necessary to undertake certain procedures that call for reversal of flow through a check valve.

SUMMARY

Accordingly, it may be beneficial to provide a valve device with bypass structure in which the valve member can be unseated so that removal and re-insertion of the valve device can be avoided if two-way flow through the valve device is desired.

According to one aspect of the disclosure, a valve device can include a housing defining a fluid passage, and a valve member movably mounted with respect to the housing, wherein the valve member is movable between a closed state position and an opened state position. A bypass device can include an input structure, a motion conversion structure, and an output structure, wherein the input structure includes a portion configured to resiliently move if a valve opening input force is applied to the input structure in an input direction. The motion conversion structure can be configured to convert the valve opening input force into a motion of the output structure in an output direction that is non-parallel to the input direction. The output structure can be configured to move the valve member if the motion conversion structure is displaced in the input direction.

According to another aspect of the disclosed subject matter, a delivery system for infusing a fluid into a patient can include the valve device according to the above-described first aspect of the disclosure. The system can include a first conduit having a first end configured to be connected in fluid communication with a source of fluid, and a second end configured to be connected to the valve device. The system can also include a second conduit having a proximal end and a distal end, the proximal end of the second conduit configured to be connected to the valve device and the distal end of the second conduit configured to be connected in fluid communication with the patient.

According to another aspect of the disclosed subject matter, a method for operating a valve device located on a patient infusion line can include providing a valve device including a bypass structure. The method can also include moving at least a first portion of the bypass structure in a first direction, and displacing a second portion of the bypass structure in a second direction in response to moving the first portion of the bypass structure, the second direction being non-parallel to the first direction, wherein displacing of the second portion of the bypass structure causes the valve device to open and thus allows fluid to flow through the valve device.

BRIEF DESCRIPTION OF THE DRAWINGS

The disclosed subject matter of the present application will now be described in more detail with reference to exemplary embodiments of the apparatus and method, given by way of example, and with reference to the accompanying drawings, in which:

FIGS. 2A and 2B are a cross-sectional view of an exemplary embodiment of a valve device in accordance with the disclosed subject matter, in a non-actuated state and an actuated state, respectively.

FIG. 5 is a table of widths based on a plurality of radii and a plurality of lengths for exemplary motion conversion structures as shown in FIG. 3.

FIGS. 10A and 10B are a cross-sectional view of another exemplary embodiment of a valve device in accordance with the disclosed subject matter, in an unlocked state and a locked state, respectively.

DETAILED DESCRIPTION OF EXEMPLARY EMBODIMENTS

Figure 1:
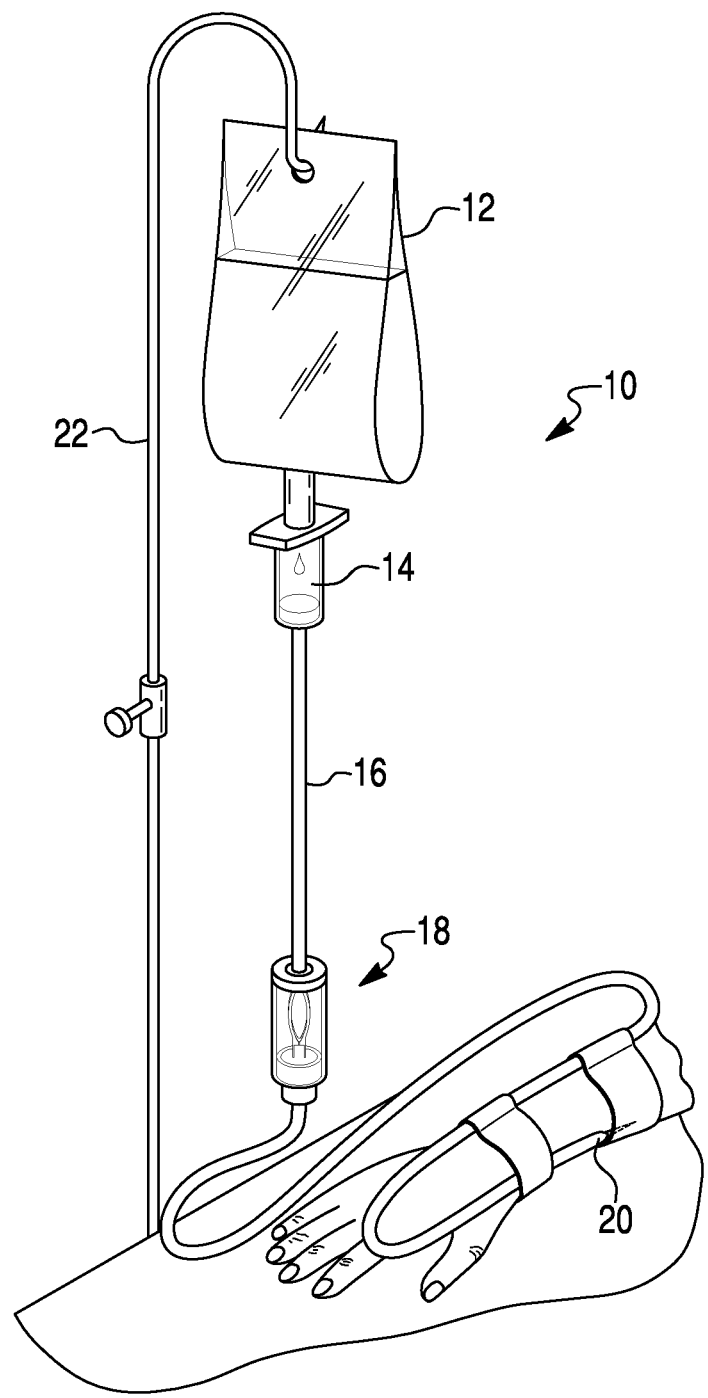
FIG. 1 is a perspective view of an exemplary embodiment of a delivery system in accordance with the disclosed subject matter.

FIG. 1 is a perspective view of one exemplary embodiment of a delivery system 10 made in accordance with principles of the disclosed subject matter. The system 10 can be used in any suitable configuration to permit the delivery of fluid (i.e., gas or liquid) from a source of the fluid (which can be from a bag fluid source 12, an infusion pump, or other known fluid source) to a fluid receiving site. In an exemplary embodiment depicted in FIG. 1, the system 10 can be configured to deliver fluids to a patient. The patient can be a human patient or an animal patient. However, the system 10 can be configured to deliver fluid to a machine or other inanimate object, as desired.

The system 10 can include a fluid source 12, a first connector 14, conduit 16, a valve device 18, and a second connector 20. The first connector 14 can be configured to connect the conduit 16 in fluid communication with the fluid source 12. The second connector 20 can be configured to connect the conduit 16 in fluid communication with the fluid receiving site. If the system 10 is configured to deliver fluid to a patient, the system 10 can include any appropriate number of additional components, such as but not limited to, a catheter, a filter, a pump (e.g., an infusion pump), a clamp, a needless access port, an injection port, a female adapter, a male adapter, a connector, a stopcock, a luer activated stopcock, a plated stopcock, a manifold, and the like. One or more of each of these exemplary components can be included with the system 10, as desired.

It should be understood that the terms "proximal" and "distal" used throughout this description represent an orientation relative to the fluid source 12 and that these terms are not limited to the medical arts usage of "proximal" and "distal." That is, "proximal" references a direction from the component or component portion that is toward the fluid source 12 and "distal" references a direction from the component or component portion that is away from the fluid source 12. For example, as viewed in FIG. 2A, the proximal end of the valve device 18 can be the end at the top of FIG. 2A and the distal end of the valve device 18 can be the end at the bottom of FIG. 2A.

The valve device 18 can selectively open and close fluid communication between the fluid source 12 and the second connector 20. The valve device 18 can be configured as a normally closed valve device where fluid communication through the valve device 18 is normally closed and an input is applied to the valve device 18 to open fluid communication through the valve device 18. In an alternate embodiment, the valve device 18 can be configured as a normally opened valve device where fluid communication through the valve device 18 is normally opened and an input is applied to the valve device 18 to close fluid communication through the valve device 18. The input can be caused by a sufficient pressure differential so as to automatically open the valve, or can be caused by a mechanical input as described herein. In another alternate embodiment, the valve device 18 can be configured with a valve member that can be positioned at any location between a closed position and an opened position. The valve device 18 can be positioned in the system 10 at any location between the first connector 14 and the second connector 20. The valve device 18 can be the last of any of the additional components of the delivery system 10 discussed above that is positioned proximal to the second connector 20.

Figure 2A:
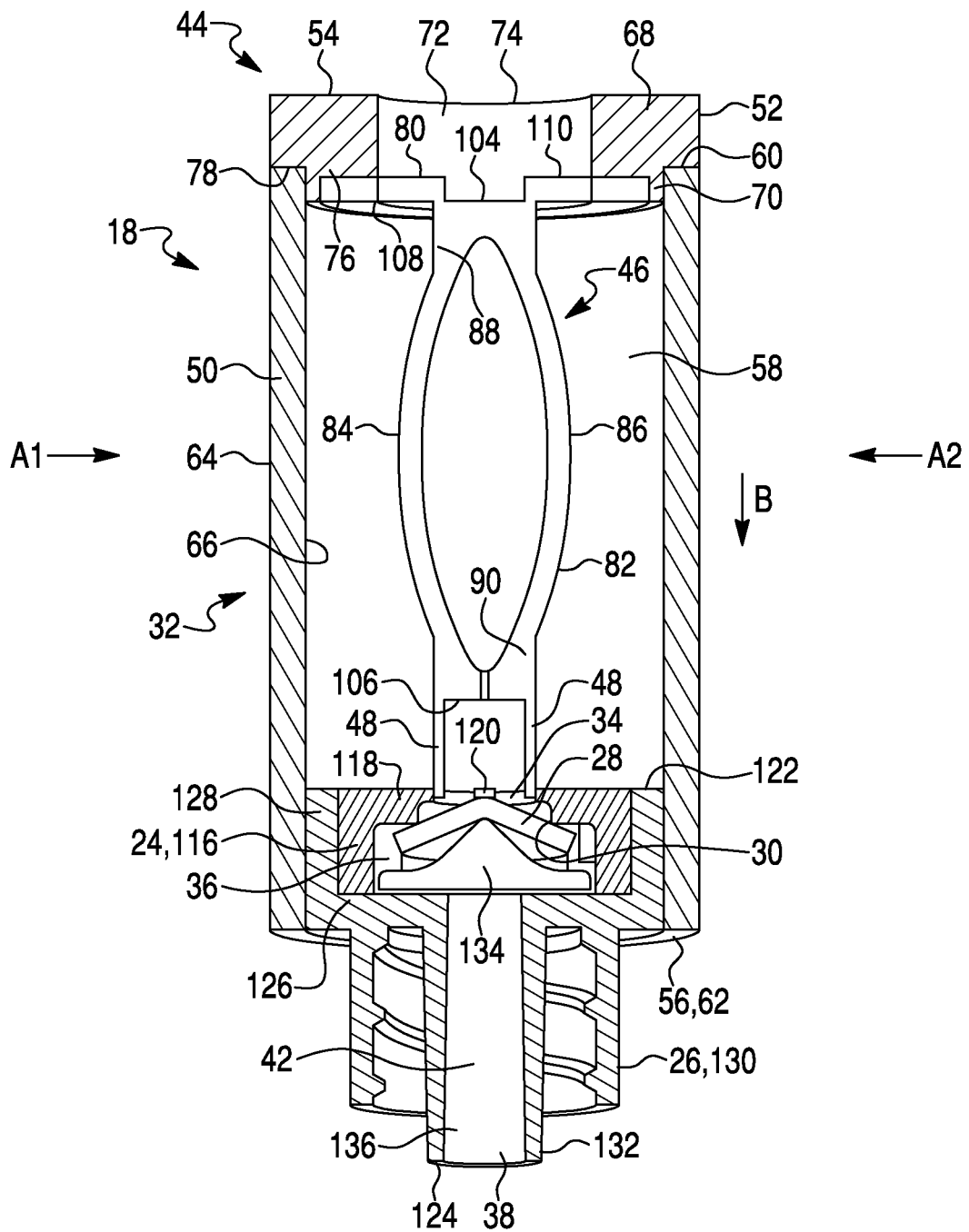

FIG. 2A is a cross-sectional view of an exemplary embodiment of the valve device 18 made in accordance with principles of the disclosed subject matter in a non-actuated state. The valve device 18 can include a first housing part 24, a second housing part 26, a valve member 28, a valve seat 30 and a bypass assembly 32. The first housing part 24 can be in selective fluid communication with the second housing part 26. The valve member 28 can be configured to selectively open and close fluid communication between the first housing part 24 and the second housing part 26. In one exemplary embodiment, the bypass assembly 32 can be configured to act on the valve member 28 to cause the valve member 28 to disengage from the valve seat 30, thereby selectively opening fluid communication between the first housing part 24 and the second housing part 26. In another exemplary embodiment, the bypass assembly 32 can be configured to act on the valve member 28 to cause the valve member 28 to engage the valve seat 30, thereby selectively closing fluid communication between the first housing part 24 and the second housing part 26. Further details of the operation of the valve member 28 and the bypass assembly 32 will be described below.

The first housing part 24 can be connected to the second housing part 26. In an alternate embodiment, the first housing part 24 and the second housing part 26 can be integrally formed as a single, continuous, homogenous unit. The first housing part 24 and the second housing part 26 can be formed from any material compatible with the fluid intended to flow through the valve device 18. In an exemplary embodiment, the first housing part 24 and the second housing part can be formed from a plastic material such as but not limited to polycarbonate. If the first housing part 24 is formed as a separate element from the second housing part 26, then these housing parts 24, 26 can be joined by any suitable connection such as, but not limited to, a friction fit, an adhesive, a sonic weld, a friction weld, and a threaded connection with or without a separate seal.

The first housing part 24 can include a proximal opening 34 in the proximal end of the first housing part 24, a distal opening in the distal end of the housing part 24, and a first fluid passage 36 extending from the proximal opening 34 of the first housing part 24 to the distal opening of the first housing part 24. The second housing part 26 can include a proximal opening in the proximal end of the second housing part 26, a distal opening 38 in the distal end of the second housing part 26, and a second fluid passage 42 extending from the proximal opening of the second housing part 26 to the distal opening 38 of the second housing part 26.

In an exemplary embodiment, the valve seat 30 is formed in the first fluid passage 36, but it is within the scope of the presently disclosed subject matter to form the valve seat 30 in the second fluid passage 42 even though such an embodiment is not illustrated. The valve member 28 can be movably mounted at a location between the first housing part 24 and the second housing part 26. The valve member 28 can move into and out of engagement with the valve seat 30. If the valve member 28 is moved into engagement with the valve seat 30, the valve member 28 can close fluid communication between the first housing part 24 and the second housing part 26. If the valve member 28 is moved out of engagement with the valve seat 30, the valve member 28 can open fluid communication between the first housing part 24 and the second housing part 26.

The valve device 18 can be configured as a normally closed valve device in which the valve member 28 is biased into engagement with the valve seat 30 to close fluid communication between the first housing part 24 and the second housing part 26. In this exemplary embodiment, the bypass assembly 32 can act on the valve member 28 to cause the valve member 28 to open fluid communication between the first housing part 24 and the second housing part 26. Valve member 28 can also be biased such that a predetermined pressure differential (defined as crack pressure) between space 58 and space 36 allows the valve to open without the need for a mechanical bypass mechanism. The pressure can be caused by normal infusion pressure generated by gravity or pump(s).

The bypass assembly 32 can be connected to at least one of the first housing part 24 and the second housing part 26. In the exemplary embodiment illustrated in FIG. 2, the bypass assembly 32 can be connected to the second housing part 26.

The bypass assembly 32 can include a flexible input structure 44, a motion conversion structure 46 and an output structure 48. The flexible input structure 44 can be in fluid communication with the fluid source 12 and with first housing part 24 of the valve device 18. The motion conversion structure 46 and the output structure 48 can be contained within the flexible input structure 44. The motion conversion structure 46 can be configured to convert a valve opening input applied to the flexible input structure 44 in an input direction into motion of the output structure 48 in an output direction. The output direction can be non-parallel to the input direction. FIG. 2A illustrates an exemplary input direction represented by either or both of the two arrows A1 and A2, and an exemplary output direction represented by arrow B, while FIG. 2B shows the actuated state of the valve device 18 after the inputs represented by arrows A1, A2 have been applied. In particular, the output structure 48 can be connected to the motion conversion structure 46. The output structure 48 can be configured to displace the valve member 28 out of engagement with the valve seat 30 if a valve opening input is applied to the flexible input structure 44 in the input direction as shown in FIG. 2B. Thus, the bypass assembly 32 can provide a self-contained assembly that can selectively disengage the valve member 28 from the valve seat 30 as desired. As such, the disassembly and re-assembly of conventional delivery systems can be avoided and other disadvantages or characteristics, such as contamination of the system 10 with other fluid(s) and/or particles, and/or microbial organisms and/or air can be minimized or prevented.

In order to displace the valve member 28 out of engagement with the valve seat 30, a valve opening input can be applied to the flexible input structure 44. The flexible input structure 44 can be configured in any manner that permits at least a portion of the flexible input structure 44 to flex toward the motion conversion structure 46 in response to a valve opening input applied in the input direction. As shown in FIG. 2B, in an actuated state, the flexible input structure 44 is moved inward and in contact with the actuator 82 of the motion conversion structure 46 when the above-referenced input, such as a pinching force, is applied to the flexible input structure 44. This inward motion also causes the motion conversion structure 46 shown in FIG. 2B to be actuated such that first conversion member 84 is moved closer to the second conversion member 86 as compared to the state shown in FIG. 2A. Thus, the output structure 48 of the actuator 82 as shown in FIG. 2B is moved downward and along a central fluid flow axis of the device as compared to the non-actuated state shown in FIG. 2A. Furthermore, the movement of the output structure 48 and its plunger arms 112, 114 shown in FIG. 3 causes the valve member 28 to become unseated from the valve seat 30, thus opening the valve to fluid flow.

The flexible input structure 44 can extend in a first direction substantially parallel to the output direction and can include a proximal end 54, a distal end 56 spaced from the proximal end 54 in the first direction, and a fluid passage 58 extending from the proximal end 54 to the distal end 56. The proximal end 54 of the flexible input structure 44 can be configured to be connected in fluid communication (directly or indirectly) with the fluid source 12. The distal end 56 of the flexible input structure 44 can be connected to at least one of the first housing part 24 and the second housing part 26. The distal end 56 of the flexible input structure 44 can be in fluid communication (direct or indirect) with at least one of the first housing part 24 and the second housing part 26.

The flexible input structure 44 can include a resilient member 50 and a support member 52 connected to the resilient member 50.

The resilient member 50 can include a proximal opened end 60, a distal opened end 62, an outer surface 64 and an inner surface 66. The resilient member 50 can be dimensioned and/or formed from a material so that the resilient member 50 can flex toward the motion conversion structure 46 in a resilient manner in response to the valve opening input applied in the input direction. The resilient member 50 can be formed as a tubular member that can have a circular, ovoid, non-symmetrical, or polygonal cross-sectional shape. The resilient member 50 can be formed from any suitable resilient material, such as, but not limited to silicone rubber, polyethylene, polyesters, plastics, polyvinyl chloride, and other known flexible materials. The materials can be transparent, opaque, or semi-opaque. If the material is transparent or semitransparent, the user can see the exact orientation of the motion conversion structure 46 located within the resilient member 50.

As shown, the resilient member 50 can be configured as a cylindrical tubular member. In this exemplary embodiment, the motion conversion structure 46 can convert a substantially radial compression (depicted by arrows A) of the resilient member 50 into motion substantially parallel to the axial direction (depicted by arrow B) of the resilient member 50.

The support member 52 can include an annular disc portion 68, an annular projection portion 70, and a fluid passage 72. The annular projection portion 70 can extend from the distal end of the annular disc portion 68. The annular projection portion 70 can extend into the resilient member 50 and can engage the inner surface 66 of the resilient member 50 adjacent the proximal opened end 60 of the resilient member 50.

The fluid passage 72 can extend from a proximal opening 74 formed in the annular disc portion 68 at the proximal end 54 of the flexible input structure 44 to a distal opening formed in the distal end of support member 52. The fluid passage 72 can be in fluid communication with the fluid source 12. The proximal opening 74 can be configured to engage the conduit 16 directly or can be configured to receive a mating connector attached to the conduit 16. The fluid passage 72 can form a portion of the fluid passage 58 of the flexible input structure 44. In addition, the support member 52 can be considered a third housing part in combination with the first housing part 24, and second housing part 26, which all can be considered in combination to be a housing for the valve device 18.

The annular projection portion 70 can include a distal surface 76 that can engage the motion conversion structure 46. The distal surface 76 can be a recessed surface formed at the distal end of the annular projection portion 70.

The annular projection portion 70 can cooperate with the annular disc portion 68 to define a shoulder 78 to which the proximal opened end 60 of the resilient member 50 can be connected. The resilient member 50 can be connected to the shoulder 78 of the support member 52 by any appropriate connection configuration such as but not limited to an interference fit, friction welding, an adhesive, a clamp, or other known attachment structures, substances or methods.

In an alternate embodiment, the shoulder 78 can be omitted and the resilient member 50 can extend along the outer surface of the annular disc portion 68.

The rigidity of the support member 52 can be greater than both the resilient member 50 and the valve member 28 due to the structural design of the support member 52 and/or the material from which the support member 52 is formed. In an exemplary embodiment, the support member 52 can be configured as a substantially cylindrical member and can be formed of a material, such as, but not limited to silicone rubber, polyethylene, plastics, such as polycarbonate, or ceramics, metals, or combinations thereof.

The motion conversion structure 46 can include an anchor 80 and an actuator 82. The anchor 80 can be secured to (or can simply rest or bear against) a portion of the flexible input structure 44 (or housing). The actuator 82 can be connected between the anchor 80 and the output structure 48. The actuator 82 can move relative to the anchor 80 and can move relative to the flexible input structure 44 (and relative to the housing). The actuator 82 can be configured to move with respect to the flexible input structure 44 in response to movement of the flexible input structure 44. In particular, a portion of the actuator 82 that contacts the flexible input structure 44 when the flexible input structure is pinched or squeezed by a user can be configured to move with the flexible input structure 44 and, simultaneously, another portion of the actuator 82 can be caused to move relative to the flexible input structure 44 once the flexible input structure 44 is pinched beyond a predetermined distance.

The actuator 82 can include a first conversion member 84, a second conversion member 86, a proximal connector 88 and a distal connector 90. In the embodiment depicted in FIGS. 2A and 2B, the first conversion member 84 and second conversion member 86 are shown as leaf springs that run parallel with each other and are substantially (i.e., exact or almost exact) mirror images of each other. However, the first conversion member 84 and second conversion member 86 can take on various different forms, such as complicated linkage mechanisms (as described in more detail below), coil springs, flexible bladder/pneumatic systems, electrically actuated movement conversion structures, etc.

Figure 3:
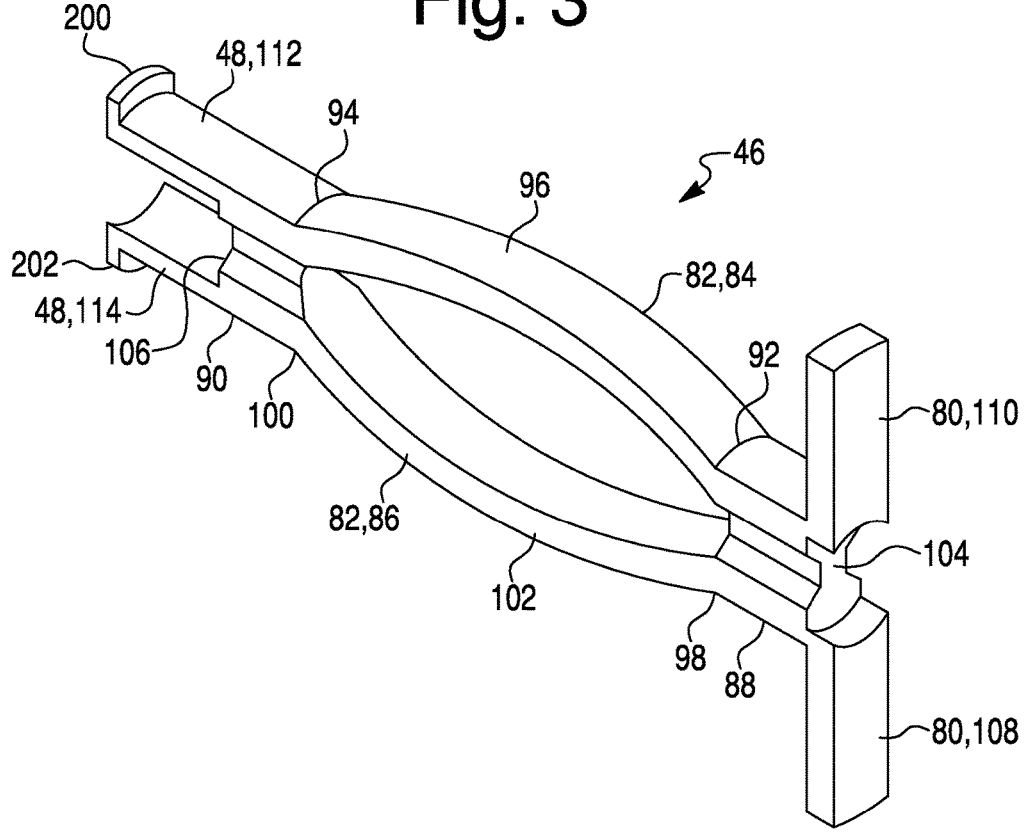
FIG. 3 is a perspective view of portions of a bypass device in accordance with the disclosed subject matter.

As shown in FIG. 3, the first conversion member 84 can include a proximal end 92, a distal end 94, and a central portion 96. The central portion 96 can extend in an arc from the proximal end 92 to the distal end 94.

The second conversion member 86 can include a proximal end 98, a distal end 100, and a central portion 102. The central portion 102 can extend in an arc from the proximal end 98 to the distal end 100.

The proximal connector 88 can include a proximal face 104 and the distal connector 90 can include a distal face 106. The output structure 48 can be connected to and can extend from the distal face 106 of the distal connector 90. The anchor 80 can be connected to and can extend from the proximal face 104 of the proximal connector 88.

The anchor 80 can include a first arm 108 and a second arm 110. The first arm 108 can extend in an opposite direction in which the second arm 110 extends. The first arm 108 and the second arm 110 can extend radially outward from the proximal connector 88 toward the inner surface 66 of the resilient member 50 along a common diameter of the resilient member 50. The arms 108, 110 can engage the distal surface 76 of the annular projection portion 70 of the support member 52. The arms 108, 110 can simply be located adjacent or bear against the distal surface 76, and could float in a similar manner as compared to a reflux plunger. Alternatively, although no connection is necessary, the arms 108, 110 could be connected to the distal surface by an appropriate connection, such as but not limited to, an adhesive, a friction fit, a clamp, a strap integrally formed on the annular projection portion 70, one or more tabs integrally formed with the annular projection portion 70 and extending across the distal surface 76 of the annular projection portion 70, a weld or other connective structure, material or method.

The distal surface 76 can be configured as a mating surface that matches the geometry of the arms 108, 110. In an alternate embodiment, the distal surface 76 can be formed as a circular surface recessed into the distal end of the annular projection portion 70 of the support member 52.

The output structure 48 can include a first plunger arm 112 and a second plunger arm 114. The plunger arms 112, 114 can extend away from the distal face 106 of the distal connector 90, and can be spaced apart along the distal face 106 of the distal connector 90. The plunger arms 112, 114 can be configured as arcuate walls that compliment the curvature of the proximal opening 34 in the first housing 24. The plunger walls 112, 114 can be configured to engage the valve member 28 adjacent the outer edge of the valve member 28. The plunger arms 112, 114 can have a length that permits the plunger arms 112, 114 to extend through the proximal opening 34 and into the first housing part 24 a sufficient distance to disengage the valve member 28 from the valve seat 30 if the bypass assembly 32 is actuated. Retention tabs 200, 202 can be located on each of the plunger arms 112, 114, respectively, such that the plunger arms 112, 114 are guided to ensure that they are aligned correctly on the valve member 28. The retention tabs 200, 202 also allow the arms 108, 110 to simply float and not be connected to the distal surface 76 or other portion of the support member 52.

Certain conditions can arise where it is desirable to bypass the valve device 18 in order to open fluid communication between the first housing part 24 and the second housing part 26 independently of fluid pressure that may or may not be acting on the valve member 28. For example, if the system 10 is configured to deliver fluid to a patient, either parenterally, via the alimentary canal, or other, it may be desirable to aspirate or infusate a bodily fluid away from a patient. In this exemplary situation, the bypass assembly 32 can be actuated to cause the valve member 28 to disengage from the valve seat 32, thereby opening fluid communication between the first housing part 24 and the second housing part 26.

In operation, a valve opening input can be applied to the outer surface 64 of the resilient member 50 in an input direction. By way of example only, FIG. 2A illustrates an exemplary input direction with the arrows A1, A2 where the resilient member 50 is compressed inwardly toward the motion conversion structure 46. The valve opening input can resiliently deform the resilient member 50 an amount sufficient to cause the inner surface 66 of the resilient member 50 to engage and then compress the first and second conversion members 84, 86. With the proximal end of the motion conversion structure 46 held stationary by the cooperation between the anchor 80 and the support member 52, the elasticity of the first and second conversion members 84, 86 permits the conversion members 84, 86 to expand (e.g., straighten and lengthen) toward the valve member 28. In this way, the conversion members 84, 86 can convert the inward compression of the resilient member 50 into movement of the distal connector 90 and the output structure 48 toward the valve member 28 in an output direction, which direction is non-parallel to the input direction. This displacement of the output structure 48 can cause the plunger arms 108, 110 to engage and then displace the valve member 28 out of engagement with the valve seat 30.

Thus, the normally closed back check valve device 18 can be opened by the bypass assembly 32 independently of the fluid pressure applied to the proximal face of valve member 28 Further, fluid can flow in either direction through the valve device 18.

By way of example only, FIGS. 2A and 2B illustrate an exemplary output direction with the arrow B. This exemplary output direction indicated by arrow B can be substantially perpendicular to the exemplary input direction indicated by the arrows A1, A2.

The valve member 28 can be disengaged from the valve seat 30 as long as the valve opening input force is maintained on the resilient member 50. If the valve opening input force is removed from the resilient member 50, the resiliency of the valve member 28, the actuator 82 and the resilient member 50 allow these components to return to their normal positions where the valve device 18 can return to operation as a normally closed valve device 18 (and valve member 28 blocks passage of fluid through the housing).

The valve opening input can be applied to any portion of the resilient member 50 that can compress the central portions 96, 102 of the conversion members 84, 86 an amount sufficient to displace the output structure 48 to disengage the valve member 28 from the valve seat 30. The portion of the motion conversion structure 46 displaced by the compressed portions of the resilient member 50 can be referred to as the actuation portion.

In the exemplary motion conversion structure of FIGS. 2A and 2B, the valve opening input can be applied in diametrically opposed directions relative to the cylindrical resilient member 50. In this exemplary embodiment, there can be two actuation portions. These exemplary actuation portions can correspond to the portions of the central portions 96, 102 that are diametrically opposed (with respect to the cylindrical resilient member 50) and spaced the farthest apart.

The motion conversion structure 46 can have a shape that can facilitate the flow of fluid past the motion conversion structure 46. In particular, the motion conversion structure 46 can have a cross-sectional shape that is different from the cross-sectional shape of the proximal opening 74 of the support structure 52 as viewed in a plane spanning the proximal opening 74. The motion conversion structure 46 can have a cross-sectional shape that is different from the cross-sectional shape of the proximal opening 34 of the first housing part 24 as viewed in a plane spanning the proximal opening 34. Further, the cross-section area of the motion conversion structure 46 measured in the aforementioned cross-sectional plane can be substantially less than that of the cross-sectional area of each of the proximal openings 34, 74 measured in the aforementioned cross-sectional plane.

The first arm 108 and the second arm 110 of the anchor 80 can each terminate at a respective end. The ends of the arms 108, 110 can cooperate with the proximal face 104 of the proximal connector to define a recess. The recess can be centered on the fluid passage 72 of the support member 52. The recess can participate in facilitating the flow of fluid past the motion conversion structure 46.

The proximal connector 88 and the distal connector 90 can include concave sides that extend from the proximal end to the distal end of each connector 88, 90. Each concave side can include three abutting planar surfaces. For example, a cross section taken normal to a longitudinal axis of the motion conversion structure 46 at connector 88 and at connector 90 can be configured as a substantially hourglass shape. The cross-sectional shape at connector 88 and at connector 90 can be configured to allow for greater fluid flow past the motion conversion structure 46 and through the valve. In an alternate embodiment, each concave side at connector 88 and 90 can include at least two abutting planar surfaces. The concave sides can participate in facilitating the flow of fluid past the motion conversion structure 46. In another alternate embodiment, each concave side can be configured as a continuously curved surface. In another alternate embodiment, each concave surface can include a plurality of abutting curved surfaces.

The actuator 82 can have a maximum width that is less than the diameter of the inner surface 66 of the resilient member 50. In the exemplary embodiment of FIG. 3, the actuator 82 can be completely spaced from the inner surface 66. In an alternate embodiment, the actuator 82 can be in contact with the inner surface 66.

Figure 4:
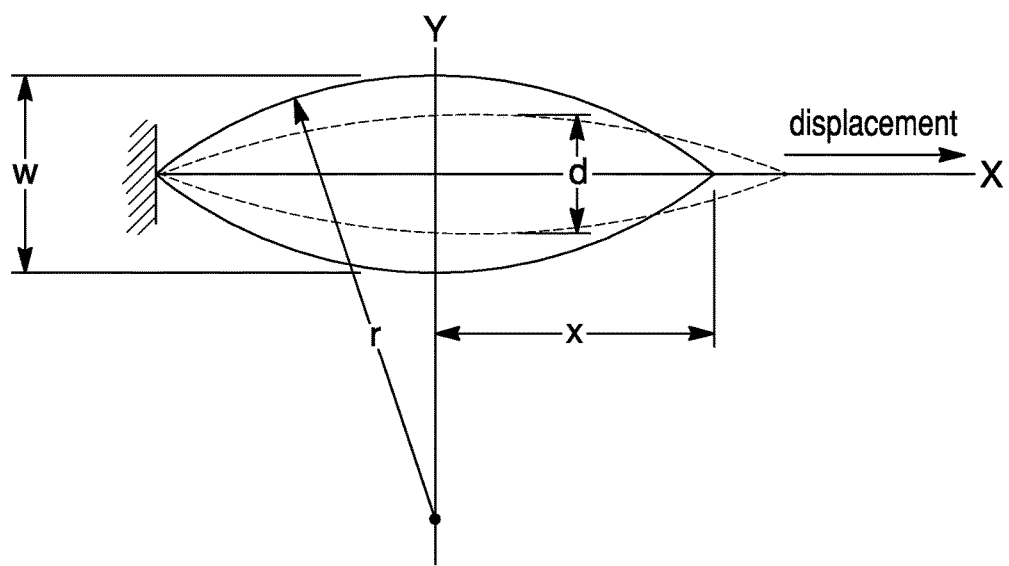
FIG. 4 is a schematic depiction of geometric properties of the bypass device of FIG. 3.

FIG. 4 schematically represents the anchor 80 and the actuator 82 of FIG. 3. Here, the actuator 82 of FIG. 3 can have a maximum width w, a length x, and a radius r. The maximum width w can be measured along an axis Y that is substantially perpendicular to an axis X that substantially bisects the actuator and extends from the proximal end to the distal end of the actuator. The length x is measured along the axis X from a point on the axis Y to the distal end of the central portion of either of the conversion members. The radius r can be a constant radius centered on the axis Y.

Figure 6:
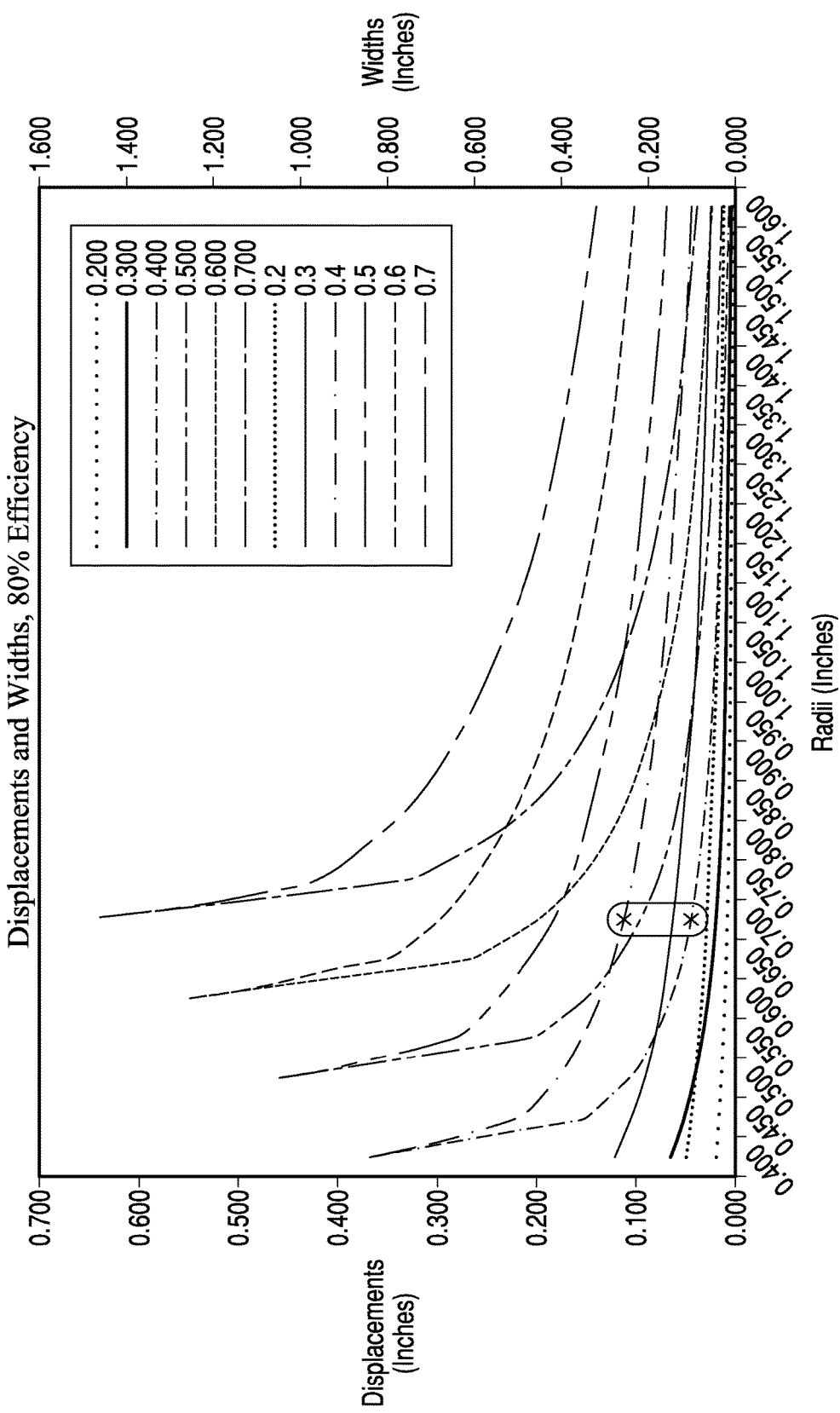
FIG. 6 is a graph showing a plurality of plots of widths and displacements versus radii for exemplary motion conversion structures as shown in FIG. 3.
Figure 7:
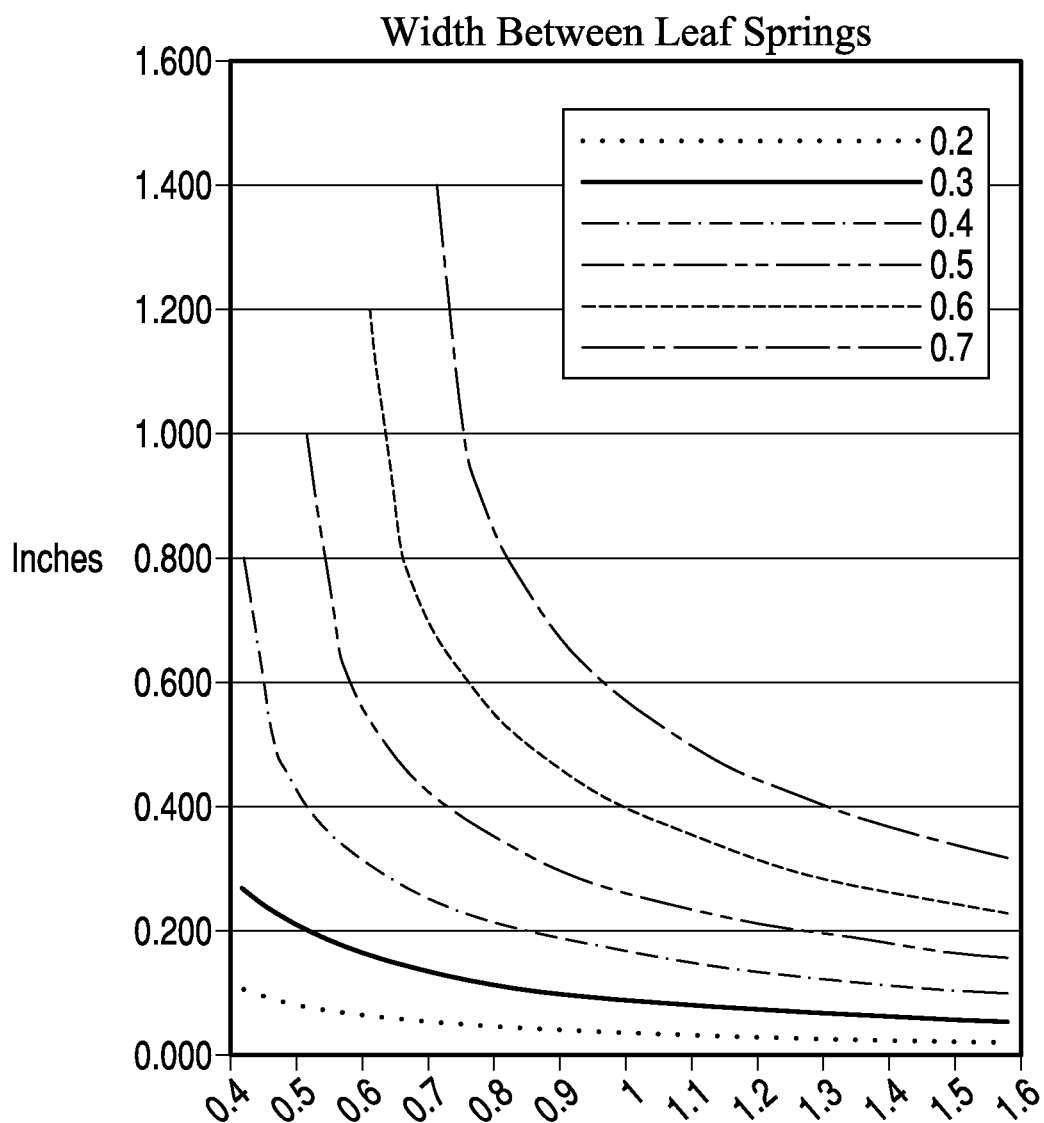
FIG. 7 is a graph showing plots of widths between conversion members of motion conversion structures as shown in FIG. 3.

In an exemplary embodiment of the valve device 18, a target displacement of the output structure 48 can be in the range of about 0.041 in. to about 0.049 in. In this exemplary embodiment of the valve device 18, the first arm 108, the second arm 110, the conversion members 84, 86, the proximal connector 88, distal connector 90 and the plunger arms 112, 114 can be integrally formed as a single, continuous, homogenous unit from various materials, such as plastics, metals, ceramics and other known materials. FIGS. 5-7 illustrate various data collections that can be used to determine advantageous values for the maximum width w, the length x and the radius r for the actuator 82. The data shown in FIGS. 5-7 is based on an 80% efficiency of the conversions members 84, 86. That is, the conversion members 84, 86 can convert 80% of the displacement in the input directions (arrows A1, A2) into displacement of the output structure 48. Based on the data represented in FIGS. 5-7, the radius r can have an optimum value in the range of about 0.650 in to about 0.700 in, the maximum width w can have an optimum valve in the range of about 0.251 in. to about 0.275 in.

As discussed above, the conversion members 84, 86 can be resiliently deformed by compression when a valve opening input force is applied to the resilient member 50 in a valve opening direction. Thus, each of the conversion members 84, 86 can move between a respective neutral position and a valve opening position. The conversion members 84, 86 can be in their respective neutral positions if the valve opening input is not applied to the resilient member 50. FIGS. 2 and 3 show the conversion members 84, 86 in the neutral position. Here, the conversion members 84, 86 are spaced apart by a neutral distance which corresponds to the maximum width w less the thickness of each conversion member measured along the axis Y. FIG. 4 schematically illustrates the conversion members in the valve opening positions in dashed lines and spaced apart by the valve opening distance d. Likewise, 2B graphically depicts the valve open position.

Accordingly, the bypass assembly 32 can open the valve device 18 independently of the fluid pressure acting on the valve member 28. Further, due to the resilient deformability of the resilient member 50, the actuator 82 and the bias acting on the valve member 28, the valve device 18 can be easily returned to normally closed operation if the valve opening input is removed. This feature can be advantageous for a valve device 18 used in a fluid delivery system 10 that can supply fluid to a patient.

Figure 8:
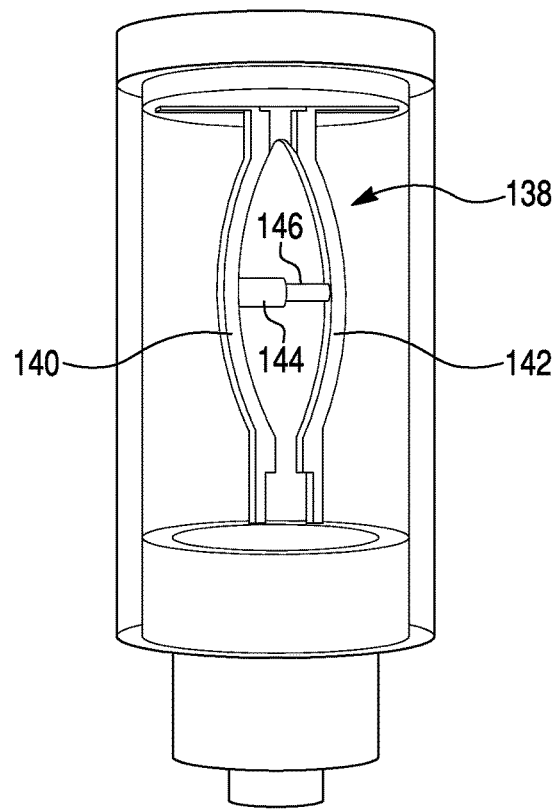
FIG. 8 is perspective view of another exemplary embodiment of a valve device in accordance with the disclosed subject matter.
Figure 9:
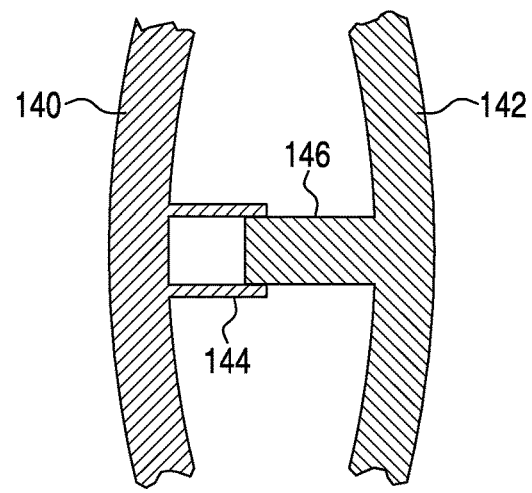
FIG. 9 is an enlarged cross-sectional view of a portion of the exemplary embodiment of FIG. 8.

As discussed above, the conversion members 84, 86 can be compressed by the valve opening input. FIGS. 8 and 9 illustrate an alternate embodiment of a motion conversion structure 138. In this embodiment, the motion conversion structure 138 can be configured substantially as described above with respect to FIGS. 2A-7. Additionally, the motion conversion structure 138 can include a stop structure configured to guide and/or limit the amount of deformation of the conversion members 140, 142. The stop structure can include a socket 144 and a pin 146. The socket 144 can be connected to the first conversion member 140. The pin 146 can be connected to the second conversion member 142. As shown in FIG. 9, the socket 144 can be hollow and the pin 146 can slide within the socket 144. The length of the pin 146 can be set to correspond to a maximum desired compression length of the conversion members 140, 142. In an alternate embodiment, a pin 146 (or other extending structure) can be provided without a complimentary socket 144. The pin 146 can be configured to be guided by another different structure other than a socket 144, and can simply run along a surface, or be guided within an opening, or be limited in movement by another structure if the pin 146 is moved outside a prescribed range of movement.

Figure 10A:
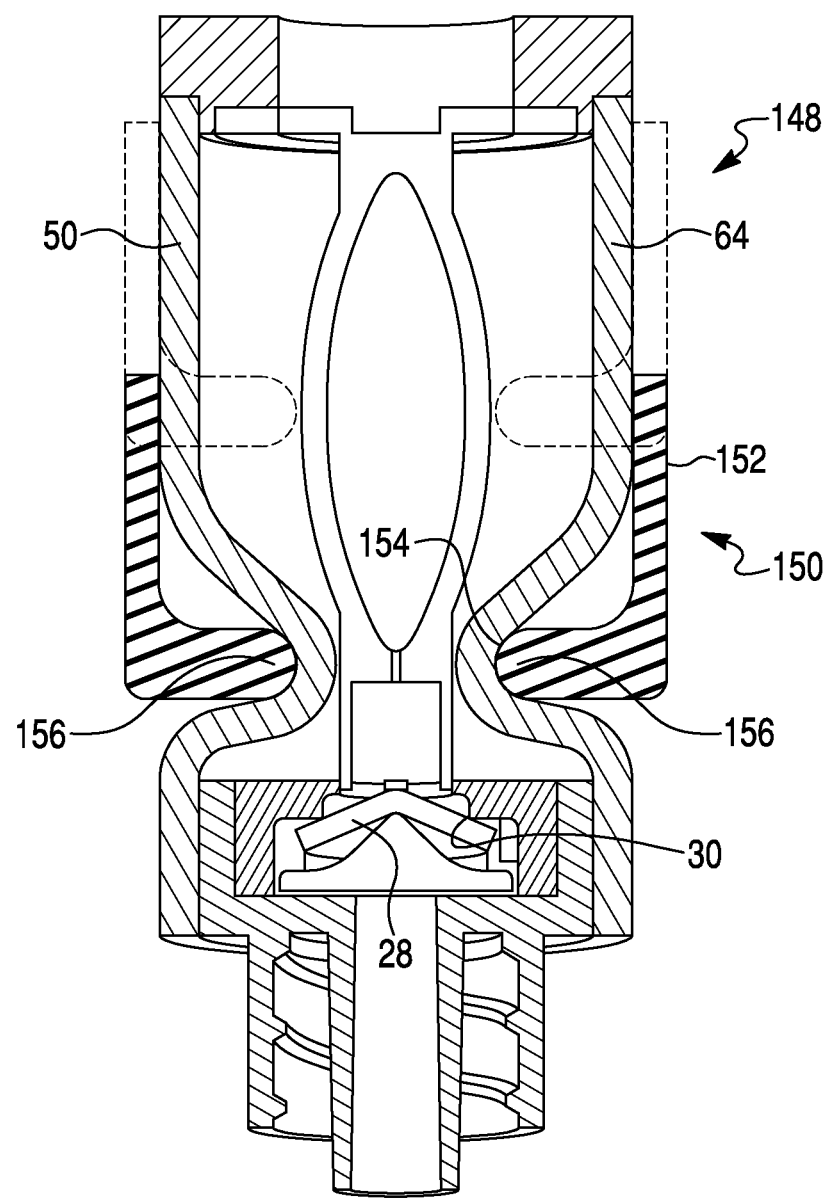

FIGS. 10A and 10B illustrate an alternate embodiment of a bypass assembly 148, in an unlocked state and a locked state, respectively. The bypass assembly 148 can disengage the valve member 28 from the valve seat 30 if a valve opening input is applied to the resilient member 50 in the valve opening direction. In many respects, the bypass assembly 148 can be configured substantially as described above with respect the bypass assembly 32 shown in FIGS. 2A-7. However, the bypass assembly 148 can include a lock structure 150. The lock structure 150 can be movable relative to the resilient member 50 between a locked position (FIG. 10B) and an unlocked position (FIG. 10A) with the lock structure 150 also shown in the locked position via dotted lines in FIG. 10A. The locked and unlocked position of the lock structure 150 can be located at different positions along a longitudinal or central axis of the resilient member 50. The bypass assembly 148 can disengage the valve member 28 from the valve seat 30 if the lock structure 150 is in the locked position (uppermost position shown in dotted lines in FIG. 10A), and the bypass assembly 148 is configured to permit the valve member 28 to engage the valve seat 30 if the lock structure 150 is in the unlocked position (lowermost position shown in FIG. 10A).

The lock structure 150 can be mounted on the flexible input structure 44. The lock structure can include a sleeve 152, a first projection 154 and a second projection 156.

The sleeve 152 can be slidably mounted on the outer surface of the resilient member 50. The inner surface of the sleeve 152 can be complimentary to the outer surface 64 of the resilient member 50. The sleeve 152 can be configured, for example, as a hollow cylinder.

The projections 154, 156 can extend from the sleeve 152 inwardly of the sleeve 152 and toward the flexible input structure 44. The friction between the projections 154, 156 and the outer surface 64 of the resilient member 50 can hold the lock structure 152 in place with respect to the resilient member 50. The projections 154, 156 can be spaced apart by a distance sufficient to displace the conversion member 84, 86 to be spaced apart by a valve opening distance if the lock structure 150 is in the locked position shown in phantom in FIG. 10A. The projections 154, 156 can be diametrically opposed, and can be configured as opposed cams.

Figure 11:
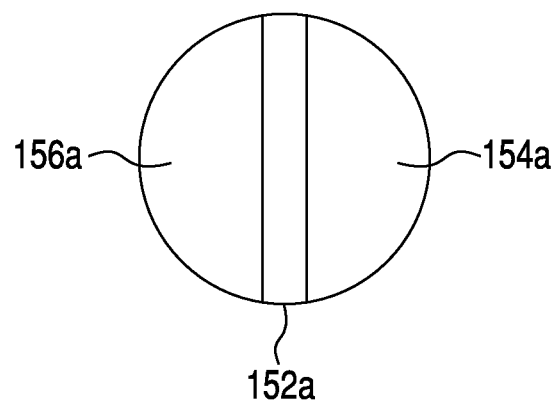
FIG. 11 is an end view of the lock structure shown in FIG. 10A.

FIG. 11 shows a bottom view of an exemplary embodiment of a sleeve 152a that can include a first projection 154a and a second projection 156a. The sleeve 152a can have a circular cross-sectional shape. The projections 154a, 156a can extend in a radially inward direction of the sleeve 152a. The projections 154a, 156a can be spaced apart by a distance sufficient to displace the conversion members 84, 86 by a valve opening distance if the lock structure 150 is in the locked position shown in phantom in FIG. 10A. The projections 154a, 156a can have a semi-circular shape as viewed in FIGS. 10A, 10B, and 11.

Figure 12:
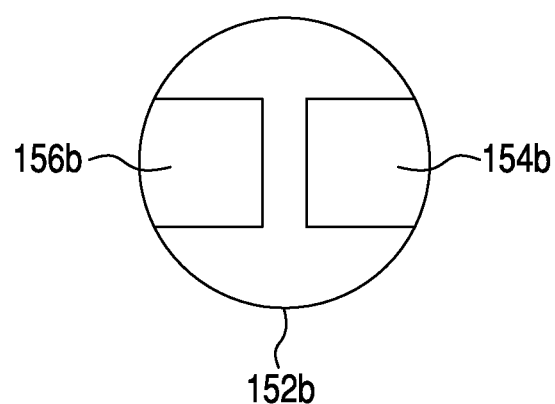
FIG. 12 is an end view of another exemplary embodiment of the lock structure of FIG. 10A.

FIG. 12 shows a bottom view of a second exemplary embodiment of a sleeve 152b that can include a first projection 154b and a second projection 156b. The sleeve 152b can have a circular cross-sectional shape. The projections 154b, 156b can extend in a radially inward direction of the sleeve 152b. The projections 154b, 156b can be spaced apart by a distance sufficient to displace the conversion members 84, 86 by a valve opening distance if the lock structure 150 is in the locked position shown in phantom in FIG. 10A. The projections 154b, 156b can have a substantially rectangular shape with one arcuate side. The projections 154*b*, 156*b* can have a semi-circular shape as viewed in side cross section (see FIG. 10A, 10B).

The valve device 18 can be configured as a normally closed back check valve device. The type of valve device 18 also can be referred to as an anti-siphon valve device. This exemplary valve device can permit the flow of fluid through the valve device 18 in a first direction if the fluid pressure acting on the proximal side of the valve member 28 is sufficient to disengage the valve member 28 from the valve seat 30. This exemplary valve device 18 can prevent the flow of fluid through the valve device 18 in a second direction that is opposite to the first direction. Here, fluid flowing in the second direction can apply a pressure on the distal face of the valve member 28 that, in turn, can cause the valve member 28 to apply a force in addition to the biasing force acting on the valve member 28. Thus, this exemplary embodiment of the valve device 18 can check back flow of fluid through the valve device 18. These features can be advantageous for a valve device 18 used in a fluid delivery system 10 that can supply fluid to a patient.

With respect to the specific valve structure, an exemplary valve structure according to one embodiment of the disclosed subject matter can incorporate a first housing part 24 that can include a wall 116, a flange 118, and a cross bar 120. The wall 116 can be substantially cylindrical and the flange 118 can be annular. The wall 116 and the flange 118 can be formed in other geometric configurations, such as but not limited to, polygonal or irregular or any tapered shape. The flange 118 can extend inwardly from the wall 116 at the proximal end of the wall 116. The proximal opening 34 can extend through the flange 118 and can cooperate with the inner surface of the wall 116 to define a fluid passage through the first housing part 24. The valve seat 30 can be formed along an inner edge of the flange 118. The cross bar 120 can extend across the proximal opening 34 of the annular flange 118 at the proximal end of the first housing part 24. The proximal opening 34 can be substantially cylindrical and the cross bar 120 can be sized to obstruct a minority portion of the proximal opening 34. As will be discussed in further detail below, the cross bar 120 can guide the valve member 28 so that the valve member 28 can be maintained in a position substantially centered about the valve seat 30.

The second housing part 26 can include a proximal end 122, a distal end 124, a central portion 126, a first wall 128, a second wall 130 and a third wall 132, a valve support member 134, and a fluid passage 136.

The central portion 126 can include an opening that can extend through the central portion 126. This opening can be in fluid communication with at least a portion of the first housing part 24 bounded by the inner surface of the wall 116. The central portion 126 can be annular. In an alternate embodiment, the central portion 126 can be formed in other geometric configurations, such as but not limited to, polygonal, non-symmetrical, etc.

The first wall 128 can extend from the central portion 126 to the proximal end 122 of the second housing part 26. The first wall 128 can be configured to engage the outer surface of the wall 116 of the first housing part 24. The first wall 128 can be substantially cylindrical or can be formed in other geometric configurations, such as but not limited to, polygonal or irregular or any tapered shape, etc.

The second wall 130 can extend from the central annular portion 126 toward the distal end 124 of the second housing part 26. The second wall 130 can be substantially cylindrical or can be formed in other geometric configurations, such as but not limited to, polygonal or irregular or any tapered shape, etc. The second wall 130 can include internal threads configured to engage a connector secured to a length of the conduit 16. In an alternate embodiment, the second wall 130 can be omitted.

The third wall 132 can extend from the central portion 126 to the distal end 124 of the second housing part 26. The third wall 132 can be configured to engage a mating connector secured to a length of conduit 16 or can be configured to directly engage the length of conduit 16. The third wall 132 can be substantially cylindrical and the outer surface of the third wall 132 can be tapered from the central portion 126 toward the distal end 124 of the second housing part 26. In an alternate embodiment, the third wall 132 can be formed in other geometric configurations, such as but not limited to, polygonal or irregular, with or without a taper, etc.

The third wall 132 can include the distal opening 38. The fluid passage 136 can extend from the opening in the central portion 126 to the distal opening 38 in the second housing part 26.

The valve support member 134 can be dimensioned to permit fluid communication between the opening in the central portion 126 and the internal portion of the first housing part 24 surrounded by the inner surface of the wall 116. The valve support member 134 can be substantially triangular in shape with a rounded tip engaging the valve member 28. The valve support member 134 can be formed in other geometric configurations, such as but not limited to, polygonal or arcuate, etc.

The valve member 28 can be a solid flat disc including a proximal face and a distal face. The valve member 28 can be resilient and can be formed of a material such as but not limited to plastic, including silicone rubber, etc. The proximal face of the valve member 28 can engage the cross bar 120 and a distal face engaging the valve support member 134. The dimensions of the valve member 28 and the spatial relationship between the valve seat 30, the cross bar 120 and the valve support member 134 can cause the valve member 28 to deform in a resilient manner from the flat disc shape to the deformed shape depicted in FIG. 2A. This resilient deformation of the valve member 28 can generate a biasing force in the valve member 28 that can bias the valve member 28 into engagement with the valve seat 30. The valve member 28 can close fluid communication between the first housing part 24 and the second housing part 26 when the valve member 28 engages the valve seat 30. Hence, the valve device 18 can be referred to as a normally closed back check valve device.

The valve member 28 can be configured to resiliently deform further in response to a fluid pressure acting on the proximal face of the valve member 28 if this fluid pressure is greater than or substantially equal to a predetermined threshold pressure. This further resilient deformation can cause the valve member 28 to disengage from the valve seat 30 thereby opening fluid communication between the first housing part 24 and the second housing part 26. This further resilient deformation of the valve member 28 can impart a bias within the valve member 28 that can cause the valve member 28 to re-engage the valve seat 30, thereby closing fluid communication between the first housing part 24 and the second housing part 26, if the fluid pressure acting on proximal face of the valve member 28 is less than the predetermined threshold pressure or if the fluid pressure is removed from the proximal face of the valve member 28.

The cross bar 120 and the valve support member 134 can be configured to press against the valve member 28 so that the rounded tip of the valve support member 134 can form an indentation in the distal face of the valve member 28. This indentation can positively restrain the valve movement from lateral movement toward the inner surface of the wall 116 of the first housing part 24. In an alternate embodiment, if any lateral movement should occur, or if during assembly the valve member 28 happens to move slightly off center so that one peripheral edge tends to engage against the inner surface of the wall 116 of the first housing part 24, longitudinal ribs can be formed on the inner surface of the wall 116 of the first housing part 24 to prevent or at least minimize frictional binding of the valve member 28 against the inner surface of the wall 116 of the first housing part 24.

The fluid source 12 can include a fluid useful in the treatment of a patient such as but not limited to saline, vitamins, nutrients, medicine and medicament. The fluid source 12 can be suspended from a support stand 22 at an appropriate elevation to promote the desired flow of the fluid from the fluid source 12 to the patient.

The first connector 14 can be configured to be connected in direct or indirect fluid communication with the fluid source 12. In an exemplary embodiment in which the system 10 is configured to deliver fluids to a patient, the connector 14 can include a chamber and a spike extending from the chamber. The spike can be configured to penetrate the fluid source and to form a fluid tight seal around the spike. This exemplary embodiment of the connector 14 can be configured to regulate the flow of fluid from the fluid source 12 through the connector 14. As such, this exemplary embodiment of the connector 14 can be referred to as a drip chamber or as a flow regulating chamber.

The conduit 16 can be configured as flexible tubing or as a rigid pipe. In the exemplary embodiment of FIG. 1, the conduit 16 can be configured as flexible tubing. A first length of tubing 16 can include a proximal end connected to the first connector 14 and a distal end in direct or indirect fluid communication with the valve device 18. A second length of tubing 16 can include a proximal end in fluid communication with the valve device 18 and a distal end in fluid communication with the second connector 20.

If the system 10 is configured to deliver fluids to a patient, the second connector 20 can be configured to receive a catheter 21 or the second connector 20 can be configured as a catheter 21. The catheter 21 can be configured for fluid communication with the patient. The catheter 21 can be configured to infuse fluid into the patient parenterally or via the alimentary canal or via other known methods and structures for infusing patients.

Figure 13:
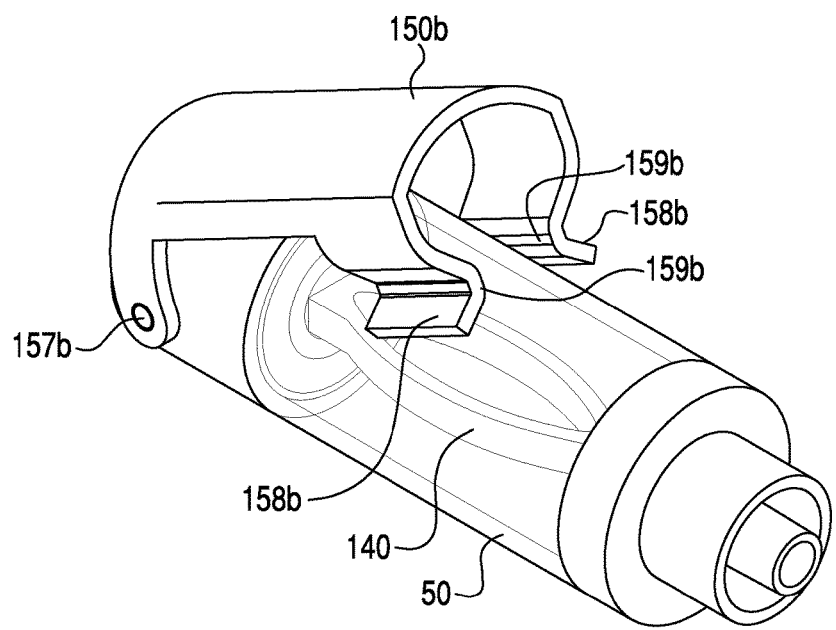
FIG. 13 is a perspective view of another exemplary embodiment of a delivery system in accordance with the disclosed subject matter.

FIG. 13 is a perspective view of another embodiment of a bypass assembly in an unlocked state. In many respects, the bypass assembly of FIG. 13 can be configured substantially as described above with respect the bypass assembly shown in FIGS. 10A-10B. However, the bypass assembly of FIG. 13 can include a different type of lock structure 150*b* that is rotatable relative to the resilient member 50 between an unlocked position, as shown, and a locked position. The lock structure 150*b* can be attached to a portion of the bypass assembly housing structure by an axle 157*b* such that the lock structure 150*b* can rotate with respect to the resilient member 50 and the motion conversion structure 140 located therein. The lock structure 150*b* can include opposing arms 158*b* that face towards each other and can be resiliently deformed towards and away from each other by virtue of their configuration and the material of the lock structure 150*b*. A cam surface 159*b* can be located on each of the arms 158*b* and configured for contact with the resilient member 50 during rotation and when the lock structure 150*b* is located in the locked state. In particular, when the lock structure 150*b* is located in the locked state, the cam surfaces 159*b* can be configured such that they pinch or otherwise actuate the motion conversion structure 138 such that valve is locked in an actuated state. The resiliency of the motion conversion structure 138 allows the valve to be locked in a non-actuated state when the lock structure 150*b* is in an unlocked state. In other words, the bypass assembly can disengage the valve member 28 from the valve seat 30 if the lock structure 150*b* is in the locked position, and the bypass assembly can permit the valve member 28 to engage the valve seat 30 if the lock structure 150*b* is in the unlocked position, as shown.

Figure 14:
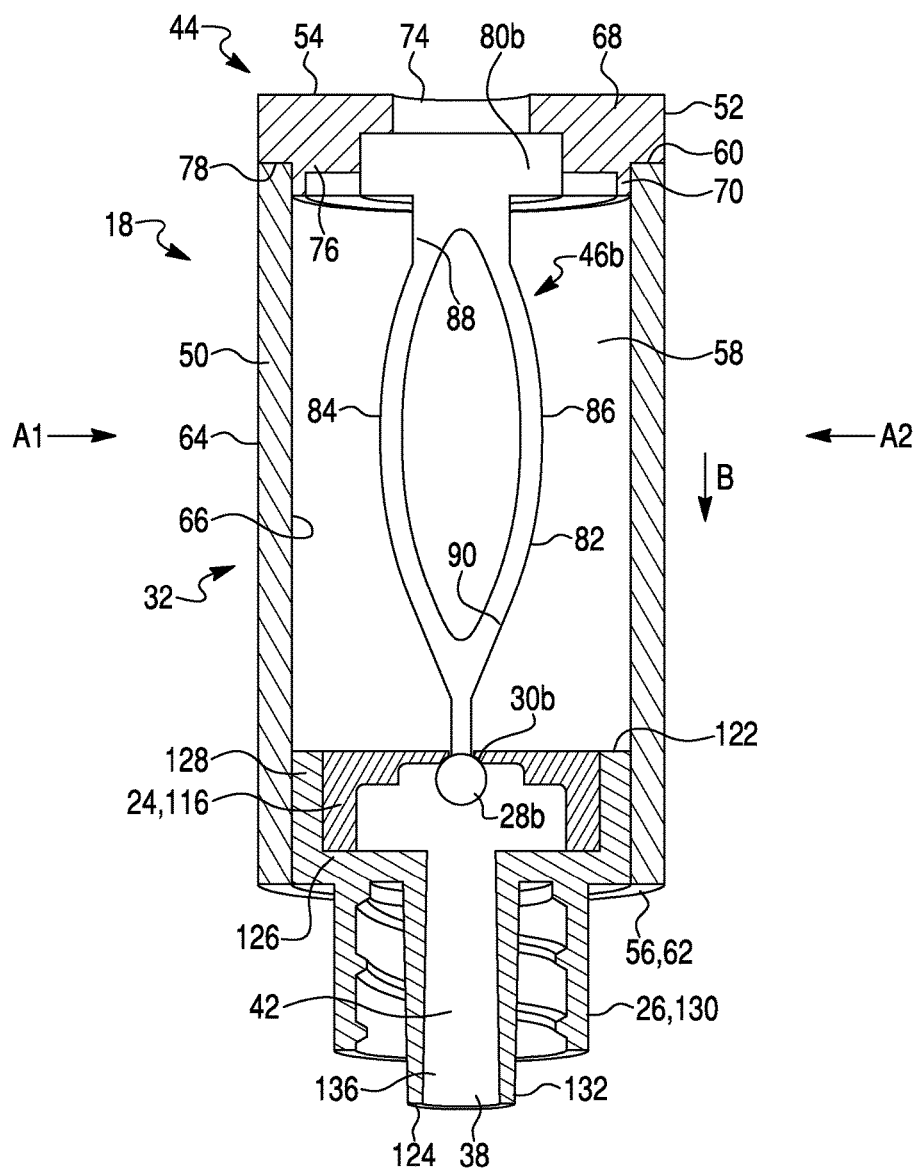
FIG. 14 is a side cross-sectional view of another exemplary embodiment of a delivery system in accordance with the disclosed subject matter.

FIG. 14 shows a side cross-sectional view of another embodiment of the valve device 18 made in accordance with principles of the disclosed subject matter in a non-actuated state. The valve device 18 can include a first housing part 24, a second housing part 26, a valve member 28*b*, a valve seat 30*b* and a bypass assembly 32. The first housing part 24 can be in selective fluid communication with the second housing part 26. The valve member 28*b* can be configured to selectively open and close fluid communication between a volume located above or upstream of the first housing part 24 and a volume located within or downstream of the second housing part 26. The bypass assembly 32 can be configured to act on the valve member 28*b* to cause the valve member 28*b* to disengage from the valve seat 30*b*, thereby selectively opening fluid communication between the volume above (or defined by an upper portion of) the first housing part 24 and the volume below (or defined by a portion of) the second housing part 26. The valve device 18 can be configured similar to the embodiment shown in FIG. 2A, and therefore a detailed description of similar structures is omitted. However, by contrast to the embodiment of FIG. 2A, the valve member 28*b* of this embodiment can be integrally formed at an end of motion conversion structure 46*b*. Thus, the number of parts in the embodiment of FIG. 14 can be reduced as compared to other embodiments.

The valve device 18 of FIG. 14 can be configured as a normally closed valve device in which the valve member 28*b* and the valve seat 30*b* are biased against each other to close fluid communication between the volume located above the first housing part 24 and the volume located at or below the second housing part 26. In this exemplary embodiment, the bypass assembly 32 can act on the valve member 28*b* to cause the valve member 28*b* to open fluid communication between the volume defined by or above the first housing part 24 and the volume defined by or below the second housing part 26. The motion conversion structure 46*b* can include an anchor 80*b* and an actuator 82. The actuator 82 can include a first conversion member 84, a second conversion member 86, a proximal connector 88 and a distal valve member 28*b*. In this embodiment, the first conversion member 84 and second conversion member 86 are shown as leaf springs that run generally parallel with each other and are substantially (i.e., exact or almost exact) mirror images of each other. However, the first conversion member 84 and second conversion member 86 can take on various different forms, such as complicated linkage mechanisms, coil springs, flexible bladder/pneumatic systems, electrically actuated movement conversion structures, etc.

The anchor 80*b* in this embodiment is secured to a portion of the flexible input structure 44 (or housing). The actuator 82 is located between the anchor 80 and the valve member 28*b* (the valve member 28*b* replacing the output structure 48 of the embodiment shown in FIG. 2A). Portions of the actuator 82 can move relative to the anchor 80 and can move relative to the flexible input structure 44 (and relative to the housing). In operation, a central portion of the actuator 82 is moved in response to movement of the flexible input structure 44. In particular, the central portion of the actuator 82 that contacts the flexible input structure 44 when the flexible input structure is pinched or squeezed by a user can be configured to move inwardly with the flexible input structure 44. Simultaneously, a distal portion of the actuator 82 can be caused to move downwardly relative to the flexible input structure 44 once the flexible input structure 44 is pinched beyond a predetermined distance.

Thus, in operation, when the actuator 82 is pinched by a force applied to opposing sides of the resilient member 50, the actuator 82 will elongate and cause the valve member 28b to move downward and away from the valve seat 30b to open the valve device and allow fluid to pass through. While certain embodiments of the invention are described above, it should be understood that the invention can be embodied and configured in many different ways without departing from the spirit and scope of the invention. For example, motion conversion structure 46 can include four links pivotally connected at their ends to form a parallelogram that mimics the general shape of the actuator 82. One of the pivot points can be fixed and the other three pivot points can be free to move relative to the fixed pivot point. A spring can bias at least one of these links. In another alternate embodiment, the motion conversion structure 46 can include any appropriate kinematic arrangement that can convert motion in a first direction into motion in a second direction that is non-parallel to the first direction, with or without a return bias. In yet another alternate embodiment, the motion conversion structure 46 can include a flexible bladder filled with a sufficient amount of fluid to allow resilient compression and re-expansion of the bladder.

In an alternate embodiment, the flexible input structure 44 can include a kinematic linkage that can include at least one link member biased in a direction that causes the flexible input structure 44 to move relative to the motion conversion structure 46. For example, the linkage can extend from a housing conduit (flexible or rigid) and attach to a motion conversion structure located within the housing conduit. Thus, the housing conduit would not be pinched in such an embodiment. Instead, a linkage member would be actuated from outside the housing conduit and would actuate the motion conversion structure located within the housing conduit.

In an alternate exemplary embodiment, the motion conversion structure and the flexible input structure can be configured to cause the output structure to move in an output direction that is any non-parallel direction relative to the input direction.

In yet another alternate embodiment the lock structure 150 can include a base, a lever and a cam. The base can be mounted on an exterior surface of the flexible input structure 44. The lever can be pivotally connected to the base. The lever can be movable between an unlocked position and a locked position. The cam can be movable with the lever. The cam can engage the base and can displace the base and a portion of the flexible input structure 44 an amount sufficient to cause the motion conversion structure 46 to displace the output structure 48 an amount sufficient to disengage the valve member 28 from the valve seat 30 if the lever is in the locked position.

In another alternate exemplary embodiment, the second housing part 26 can include a plurality of ribs formed on the proximal face of the central annular portion 126. The purpose of ribs is to assure that when the valve member 28 is completely open, an adequate space can be provided for liquid flow about the peripheral edge of the valve member 28 and above the proximal surface of the central annular portion 126.

While the subject matter has been described in detail with reference to exemplary embodiments thereof, it will be apparent to one skilled in the art that various changes can be made, and equivalents employed, without departing from the scope of the invention. All related art references described above are hereby incorporated by reference in their entirety.

What is claimed is:

1. A valve device comprising:
    a housing including a fluid passage extending along a longitudinal axis of the housing;
    a valve member movably mounted with respect to the housing such that the valve member is movable between a closed state position and an opened state position; and
    a bypass device including a flexible input structure having an inner surface facing the longitudinal axis of the housing and an outer surface facing away from the longitudinal axis of the housing, a motion conversion structure having an inner surface facing the longitudinal axis of the housing and an outer surface opposing the inner surface of the input structure and facing away from the longitudinal axis of the housing, and an output structure, wherein
    the input structure resiliently moves toward the longitudinal axis wherein the inner surface of the input structure contacts the outer surface of the motion conversion structure if a valve opening input force is applied to the input structure in an input direction,
    the motion conversion structure converts the valve opening input force into a motion of the output structure in an output direction that is non-parallel to the input direction, and
    the output structure moves the valve member if the motion conversion structure is displaced in the input direction.

2. The valve device according to claim 1, wherein the input structure includes a flexible tubular member having a proximal end and a distal end, the flexible tubular member defining a fluid passage that extends from the proximal end to the distal end.

3. The valve device according to claim 1, wherein the motion conversion structure includes:
    an anchor adjacent to a portion of the input structure; and
    an actuator connected to the anchor and connected to the output structure, the actuator being movable relative to the anchor.

4. The valve device according to claim 1, wherein the motion conversion structure includes:
    an anchor;
    a first conversion member connected to the anchor and connected to the output structure, the first conversion member being movable relative to the anchor;
    a second conversion member connected to the anchor and connected to the output structure, the second conversion member being movable relative to the anchor.

5. The valve device according to claim 4, wherein the second conversion member is movable relative to the first conversion member.

6. The valve device of claim 4, wherein
    the first conversion member includes:
        a proximal end connected to the anchor;
        a distal end connected to the output structure; and a central portion extending in an arc between the distal end of the first conversion member and the proximal end of the first conversion member.

7. The valve device of claim 6, wherein the second conversion member includes:
a proximal end connected to the anchor;
a distal end connected to the output structure; and
a central portion extending in an arc between the distal end of the second conversion member and the proximal end of the second conversion member.

8. The valve device according to claim 6, wherein the first conversion member is configured and oriented to be a substantial mirror image of the second conversion member.

9. The valve device according to claim 1, wherein the motion conversion structure includes at least one leaf spring.

10. The valve device according to claim 1, wherein the motion conversion structure includes at least two leaf springs.

11. The valve device according to claim 1, wherein the output structure includes:
a pair of plunger arms connected to and extending from a distal end of the motion conversion structure toward the valve member and which selectively engage the valve member, and the pair of plunger arms are spaced apart from each other.

12. The valve device according to claim 1, wherein the motion conversion structure and the output structure are integrally formed as a single, continuous, homogenous unit.

13. The valve device according to claim 1, wherein:
the input structure includes:
a resilient and flexible tubular member including a proximal opened end, a distal opened end, wherein a support member is connected to the proximal opened end of the resilient and flexible tubular member, and the valve member is located at the distal opened end of the resilient and flexible tubular member.

14. The valve device according to claim 1, wherein the bypass device includes:
a stop structure limiting relative motion between two portions of the motion conversion structure.

15. The valve device according to claim 1, wherein the motion conversion structure includes:
a first member; and
a second member connected to the first member and movable relative to the first member, wherein a pin is located on the second member.

16. The valve device according to claim 15, wherein a socket member is located on the first member and the socket member cooperates with the pin on the second member to guide the first member with respect to the second member during relative movement.

17. The valve device according to claim 1, further comprising:
a lock structure located adjacent the input structure and which moves relative to the input structure between a locked position and an unlocked position, the bypass device maintains the valve member in the opened state position if the lock structure is in the locked position, and the bypass device maintains the valve member in the closed state position if the lock structure is in the unlocked position.

18. The valve device according to claim 17, wherein the lock structure includes:
a sleeve slidably mounted on an exterior surface of the input structure,
a pair of opposed cams extending from the sleeve toward the input structure.

19. The valve device according to claim 17, wherein the lock structure includes:
a rotatable member having opposed cam surfaces which are rotated into the locked position.

20. The valve device according to claim 1, wherein:
the housing includes a first portion with a cross bar and a valve seat, and a second portion including a substantially triangular member; and
the valve member is a resiliently deformable disc which engages the valve seat, the cross bar and the substantially triangular member.

21. A delivery system for infusing a fluid into a patient comprising:
a valve device according to claim 1;
a first conduit having a first end connected in fluid communication with a source of fluid, and a second end connected to the valve device; and
a second conduit having a proximal end and a distal end, the proximal end of the second conduit connected to the valve device and the distal end of the second conduit connected in fluid communication with the patient.

22. A method for operating the valve device of claim 1 located on a patient infusion line, comprising:
providing the valve device of claim 1;
moving the input structure of the bypass device in the input direction;
displacing the output structure of the bypass device in the output direction in response to moving the input structure of the bypass device, the output direction being non-parallel to the input direction, wherein displacing of the output structure of the bypass device causes the valve device to open and thus allows fluid to flow through the valve device.

23. The method for operating the valve device according to claim 22, wherein:
moving the input structure of the bypass device further includes pinching the resilient tubular member.

24. The method for operating the valve device according to claim 23, wherein:
the pinching the resilient tubular member causes the motion conversion structure to extend in a direction along the longitudinal axis of the housing.

25. The method for operating the valve device according to claim 22, wherein:
displacing of the output structure of the bypass device further includes moving the valve member along the longitudinal axis of the housing to cause the valve member to become unseated.

26. The method for operating the valve device according to claim 22, wherein:
displacing of the output structure of the bypass device further includes moving a first end of the motion conversion structure along the longitudinal axis and relative to the housing, while a second end of the motion conversion structure is fixed and does not move relative to the housing.

27. The method for operating the valve device according to claim 22, further comprising:
providing the valve device with the housing having the longitudinal axis along which fluid flows, and providing the bypass device with the motion conversion structure that includes a first arm and a second arm spaced from the first arm, the first arm and second arm operatively connected to the valve member at a first end of each of the first arm and second arm, and the first arm and second arm bear against the housing at a second end of the first arm and second arm, wherein moving the input structure of the bypass device in the input direction includes moving at least one of the first arm and the second arm relative to the other of the first arm and the second arm.

28. The method for operating the valve device according to claim 27, further comprising:
providing a guide structure located adjacent at least one of the first arm and the second arm; and
using the guide structure to guide as the first arm and the second arm move relative to each other.

* * * * *